(12) United States Patent
Jeganathan et al.

(10) Patent No.: US 6,458,523 B1
(45) Date of Patent: Oct. 1, 2002

(54) HYDROQUINONE DERIVATIVES AS SCAVENGERS FOR OXIDIZED DEVELOPER

(75) Inventors: Suruliappa Gowper Jeganathan, Glen Mills, PA (US); Stéphane Biry, Village-Neuf (FR)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/869,255

(22) PCT Filed: Dec. 16, 1999

(86) PCT No.: PCT/EP99/10007

§ 371 (c)(1), (2), (4) Date: Jan. 7, 2002

(87) PCT Pub. No.: WO00/39064

PCT Pub. Date: Jul. 6, 2000

(30) Foreign Application Priority Data

Dec. 29, 1998 (EP) .............................. 98124776

(51) Int. Cl.$^7$ ................................. G03C 7/26
(52) U.S. Cl. ................. 430/564; 430/546; 430/551; 560/75; 514/257; 514/622; 564/170
(58) Field of Search ................. 430/551, 546, 430/564; 424/401; 560/75; 514/257, 622; 564/170

(56) References Cited

U.S. PATENT DOCUMENTS

| | | | | |
|---|---|---|---|---|
| 4,345,016 A | | 8/1982 | Takahashi et al. ........... 430/214 |
| 4,631,252 A | * | 12/1986 | Howell ........................ 430/551 |
| 5,449,518 A | * | 9/1995 | Junino et al. ................ 424/401 |
| 5,585,105 A | * | 12/1996 | Junino et al. ................ 424/401 |
| 5,587,173 A | * | 12/1996 | Junino et al. ................ 424/401 |
| 5,637,756 A | * | 6/1997 | Junino et al. ................ 560/75 |
| 5,667,792 A | * | 9/1997 | Junino et al. ................ 424/401 |

FOREIGN PATENT DOCUMENTS

| | | | |
|---|---|---|---|
| EP | 098241 | * | 6/1983 |
| EP | 0209118 | | 1/1987 |
| EP | 353629 | * | 7/1989 |

* cited by examiner

*Primary Examiner*—Janet Baxter
*Assistant Examiner*—Amanda C. Walke
(74) *Attorney, Agent, or Firm*—Tyler A. Stevenson

(57) ABSTRACT

New compounds of the formula I

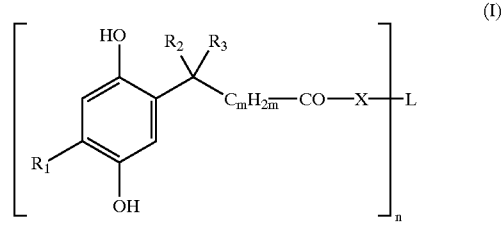

are described, wherein n is >1;

X is O or $NR_4$;

L is a n-valent linking group defined in claim 1 and $R_1$ is H, halogen, $C_1$–$C_{25}$-alkyl, $C_3$–$C_{25}$-alkenyl, unsubstituted or by $C_1$–$C_4$-alkyl substituted $C_5$–$C_8$-cycloalkyl;

$R_2$ and $R_3$ independently of each other are $C_1$–$C_4$-alkyl, or together with the carbon atom they are bonded to, form a carbocyclic $C_5$–$C_7$ ring, especially $C_5$–$C_7$ cycloalkylene; and m is 1–20, especially 2–4.

Compounds of the formula I are active as Dox-scavengers in color photographic material.

6 Claims, No Drawings

HYDROQUINONE DERIVATIVES AS SCAVENGERS FOR OXIDIZED DEVELOPER

It is well known that one of the problems associated with color photography is the diffusion of the oxidized color developer away from the light sensitive silver halide emulsion layer in which it is formed into another silver halide emulsion layer, which can result in the formation of unwanted dyes at undesired places. For instance, while being generated in the green sensitive layer and forming a magenta dye through a coupling reaction with the incorporated magenta coupler, the oxidized developer can also diffuse to the red sensitive layer thereby producing unwanted cyan dye or to the blue sensitive layer thereby producing unwanted yellow dye. This kind of color formation in the wrong layers will damage the color balance of the photographic image and thus result in poor color reproduction. One way of circumventing this problem is to incorporate oxidized developer scavengers in interlayers between the light sensitive silver halide emulsion layers. These scavengers should have additional properties such as low tendency to migrate, good stability towards aerial oxidation and high solubility in photographic oils.

Hydroquinone derivatives which are useful as scavengers for oxidized developers are e. g. described in U.S. Pat. No. 4,345,016.

This invention discloses specific hydroquinone derivatives which are very effective as scavengers for oxidized developers. These compounds show good diffusion fastness and good solubility in high boiling photographic oils. They are well suited for use in photographic elements containing pyrazolotriazole couplers as magenta dye providing compounds.

This invention describes hydroquinone derivatives of the following general formula I which can be used as scavengers for the oxidized developer (also termed hereafter Dox scavengers).

Primarily, present invention pertains to a compound of the formula I

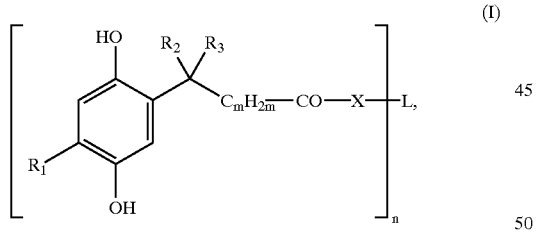
(I)

where n is always >1, for example 2–100, preferably 2–50, especially 2–30 and in particular 2–4;

X is O or $NR_4$;

if n is 2,

L is $C_2$–$C_{25}$-alkylene; $C_4$–$C_{25}$-alkylene interrupted by O, S or

$C_5$–$C_{12}$ cycloalkylene; or a group phenylene, naphthylene,

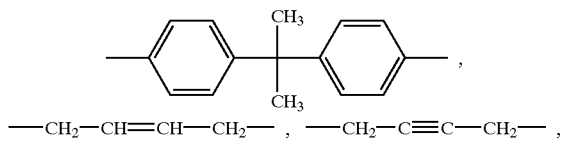

each of which may be unsubstituted or substituted by $C_1$–$C_4$-alkyl;

if n is 3, L is

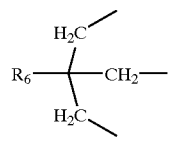

when n is 4, L is

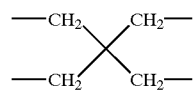

when n is >4, L is a residue of a $C_5$ or $C_6$ sugar or a polymeric chain such as a polyvalent residue of a polyvinyl alcohol;

$R_1$ is H, halogen, $C_1$–$C_{25}$-alkyl, $C_3$–$C_{25}$-alkenyl, unsubstituted or by $C_1$–$C_4$-alkyl substituted $C_5$–$C_8$-cycloalkyl;

$R_2$ and $R_3$ independently of each other are $C_1$–$C_4$alkyl, or together with the carbon atom they are bonded to, form a carbocyclic $C_5$–$C_7$ ring, especially $C_5$–$C_7$cycloalkylene;

$R_4$ is H or $C_1$–$C_{18}$alkyl, $R_5$ is H or $C_1$–$C_{18}$alkyl or $C_1$–$C_{25}$alkanoyl, $R_6$ is $C_1$–$C_{18}$alkyl or —$NR_7R_8$;

$R_7$, $R_8$ independently are $C_1$–$C_{18}$alkyl or $C_1$–$C_{25}$alkanoyl, and m is 1–20, especially 2–4.

Preferred compounds are of the formula I'

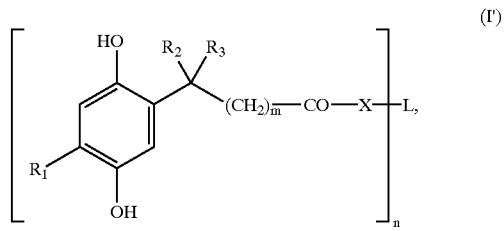
(I')

where n is 2–30;

$R_1$ is $C_1$–$C_{25}$alkyl, $R_2$ and $R_3$ independently are $C_1$–$C_4$alkyl, or together with the bonding carbon atom are $C_5$–$C_7$cycloalkylene, $R_4$ is H, $R_5$ is H, $R_6$ is $C_1$–$C_{18}$alkyl, $R_7$, $R_8$ independently are $C_1$–$C_{18}$alkyl or $C_1$–$C_{25}$alkanoyl, m is 2–4.

Examples for $C_5$ or $C_6$ sugars are:

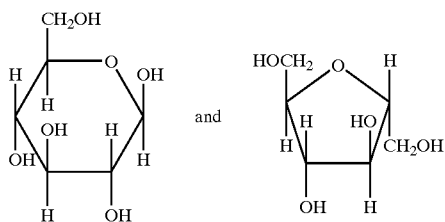

Compounds of formula I are preferably used to trap the oxidized form of a developer having the following general structure:

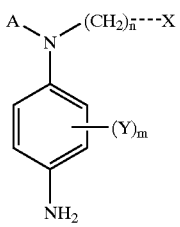

where $A = C_1-C_6$-alkyl;

$n = 1-6$;

$X$ = hydrogen, hydroxy, $C_1-C_8$-alkoxy, $-COR_9$, $-NHSO_2R_{10}$, where $R_9$ and $R_{10}$ are $C_1-C_{18}$alkoxy and $C_1-C_8$alkyl, respectively.

$Y = C_1-C_8$alkyl, $C_1-C_8$alkoxy, halogen;

$m = 0-4$.

In the above structure the preferred substituents are $A = -CH_2CH_3$ and $n=2$, $X$=hydrogen or $-NHSO_2CH_3$ or $-OH$ or $-OCH_3$, $m=0$ or $m$ 1 and $Y = -CH_3$.

Examples of these are 4-amino-N,N-diethylaniline, 3-methyl-4-amino-N,N-diethylaniline, 4-amino-N-ethyl-N-α-hydroxyethylaniline, 3-methyl-4-amino-N-ethyl-N-α-hydroxyethylaniline, 3-methyl-4-amino-N-ethyl-N-α-hydroxyethylaniline, 3-methyl-4-amino-N-ethyl-N-α-methanesulphonamidoethylaniline, 3-methyl-4-amino-N-ethyl-N-α-methoxyethyl-aniline, 3-α-methanesulphonamidoethyl-4-amino-N,N-diethylaniline, 3-methoxy-4-amino-N-ethyl-N-α-hydroxyethylaniline, 3-methoxy-4-amino-N-ethyl-N-α-methoxyethylaniline, 3-acetamido-4-amino-N,N-diethylaniline, 4-amino-N,N-dimethylaniline, N-ethyl-N-α-[α'-(α"-methoxyethoxy)ethoxy]ethyl-3-methyl-4-aminoaniline, N-ethyl-N-α-(α'-methoxyethoxy)ethyl-3-methyl-4-aminoaniline, and also the salts of such compounds, for example sulphates, hydrochlorides or toluenesulphonates.

The photographic materials according to this invention comprise a support bearing at least one layer of a light-sensitive silver halide emulsion.

Examples of color photographic materials according to this invention are color negative films, color reversal films, color positive films, color photographic paper, color reversal photographic paper, color-sensitive materials for the dye diffusion transfer process or the silver dye bleach process.

Of especial interest is a color photographic recording material comprising, on a base, at least one blue-sensitive silver halide emulsion layer containing at least one yellow dye providing compound, at least one green-sensitive silver halide emulsion layer containing at least one magenta dye providing compound, at least one red-sensitive silver halide emulsion layer containing at least one cyan dye providing compound, and customary (non light sensitive) top layer(s) and interlayers separating the light-sensitive layers. The layers of the color photographic material can be arranged in various orders as is well known in the art.

The compounds of the formula I can be contained in any of the layers of the photographic material, i.e. in any of the light sensitive silver halide emulsion layers or in a non light sensitive layer. For use as a Dox scavenger, the compound of the formula I is preferably contained in one or more non light sensitive layers. In this case, the light sensitive layers may contain a lower concentration of a compound of the formula I or none.

Compounds of formula I are preferably incorporated in an interlayer adjacent to the green-sensitive layer containing a magenta coupler. Preferred color photographic materials within this invention are those wherein the magenta coupler is of the pyrazolo-azole type, e.g. as disclosed in U.S. Pat. No. 5,538,840, column 49, line 51, until column 69, line 27, and publications cited therein; this section of U.S. Pat. No. 5,538,840 is hereby incorporated by reference. Also preferred is a color photographic material, wherein the silver halide emulsion contains at least 95 mol-% AgCl.

In general, the compounds of the formula I are contained in the photographic material in an amount from 10 to 1000 mg/$M^2$, especially from 30 to 500 mg/$m^2$.

The compounds of formula I can be milled with polymers (e.g. PVS, polyester, polyvinyl alcohol etc.) and placed in a layer thus preventing their migration to adjacent layers. Also, compounds of formula I containing a suitable functional group (e.g. ester, hydroxy) can be reacted with a polymer, e.g. a polyvinyl alcohol or polyester, in order to attach them chemically. This form will reduce their migrating tendency.

Typical bases for the photographic material include polymeric films and paper (including polymer-coated paper). Details regarding supports and other layers of color photographic recording materials can be found in *Research Disclosure*, Item 36544, September 1994.

Essential constituents of the photographic emulsion layers are binders, silver halide particles and color couplers. Details regarding the constituents of the light sensitive layers and other (non light sensitive) layers such as top layers and interlayers separating the silver halide emulsion layers can be found in *Research Disclosure*, Item 38957, September 1996.

The invention therefore also pertains to a color photographic material comprising a compound of the formula I, and to the use of a compound of the formula I as an additive in a color photographic material.

Preferred compounds of the formula I in the color photographic material of the invention or the corresponding use are as described for the process of the invention.

Compounds of present invention are of special advantage when incorporated into photographic materials containing magenta couplers of the pyrazolotriazole class.

Examples for especially suitable yellow, magenta and cyan couplers to be used in combination with compounds of the present invention are as given in U.S. Pat. No. 5,538,840, column 33, line 3, until column 73, line 34, and publications cited therein. These passages of U.S. Pat. No. 5,538,840 are hereby incorporated by reference.

The compounds of the formula I which can be used in the context of this invention can be incorporated into the color photographic recording material, on their own or together with the color coupler and with or without further additives, by pre-dissolving them in high-boiling organic solvents.

Preference is given to the use of solvents which boil at higher than 160° C. Typical examples of these solvents are the esters of phthalic acid, phosphoric acid, citric acid, benzoic acid or of fatty acids, and also alkylamides and phenols.

Further details on the structure of the color photographic material of the invention, and the components or further additives which can be employed in the novel material, can be found, inter alia, in U.S. Pat. No. 5,538,840, column 27, line 25, to column 33, line 2; and further in U.S. Pat. No. 5,538,840 from column 74, line 18, to column 106, line 16; and in U.S. Pat. No. 5,780,625, column 12, line 6, until column 57, line 6, and the publications cited in these 2 references; these passages of U.S. Pat. No. 5,538,840 and U.S. Pat. No. 5,780,625 are hereby incorporated by reference. Other useful information, how compounds of the formula I can be used in photographic material, can be taken from EP-A-0 871 066, page 10, line 10, until page 11, line 32, especially the references cited therein.

The photographic layers in the material of this invention may also include UV absorbers, which screen out the UV light and therefore protect the dyes, the couplers or other components against photodegradation. Hydroquinone compounds according to this invention may be contained in those layers where UV absorbers are present.

UV absorbers preferably to be used in the novel material or within the process of present invention include benzotriazoles, 2-hydroxybenzophenones, oxanilides, cyanoacrylates, salicylic esters, acrylonitrile derivatives, thiazolines and 2-hydroxyphenyltriazines.

GB-A-2,319,523 describes from page 49, line 21, until page 73, line 2, further details of the color photographic material, especially couplers (page 52, line 1, until page 56, line 22), UV absorbers (page 56, line 25, until page 68, line 1) and dark stabilizers (page 68, line 2, until page 73, line 2). Preferred UV absorbers of the 2-hydroxyphenyltriazine class are also described in detail, for example, in U.S. Pat. No. 5,668,200, column 1, line 30, until column 7, line 55, and as specific examples from column 26, line 31, until column 32, last line, and, together with some advantageous UV absorbers of the benzotriazole class, in U.S. Pat. No. 5,300,414, column 2 to column 10, line 54. These sections of U.S. Pat. No. 5,668,200 and U.S. Pat. No. 5,300,414 are hereby incorporated by reference.

The compounds of formula I may be used in combination with any known Dox scavengers such as hydrazines, hydrazides, hydroquinones of e.g. formula HQ-1 or HQ-2; 6-hydroxychromanes of e.g. formula A-3, hydroxylamines of e.g. formula A-4 or benzofuranones such as those described in the patent application EP-A-0 871 066.

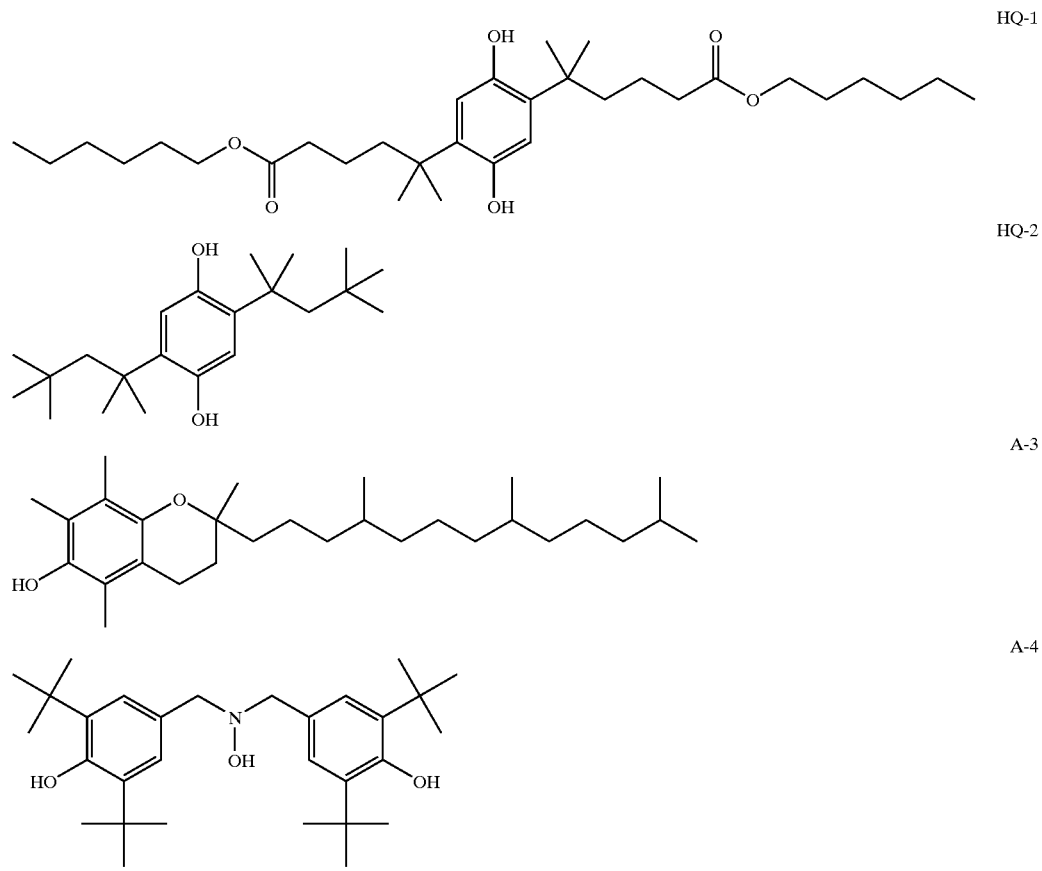

As silver halide emulsions it is possible to use customary silver chloride, silver bromide or silver iodide emulsions or mixtures thereof, such as silver chlorobromide and silver chloroiodide emulsions, in which the silver halides may have all known crystal forms. The use of silver chloride emulsions is accorded particular importance in the material of this novel process. The preparation of such emulsions and their sensitization are described in research disclosure, Item 307105, November 1989.

Compound 1 (comparison)
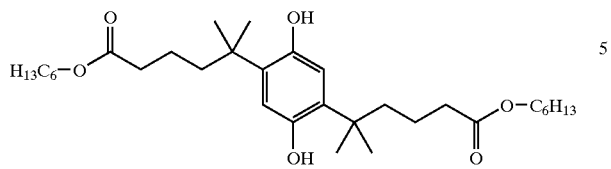
Examples of this invention are
Compound 2 (invention)
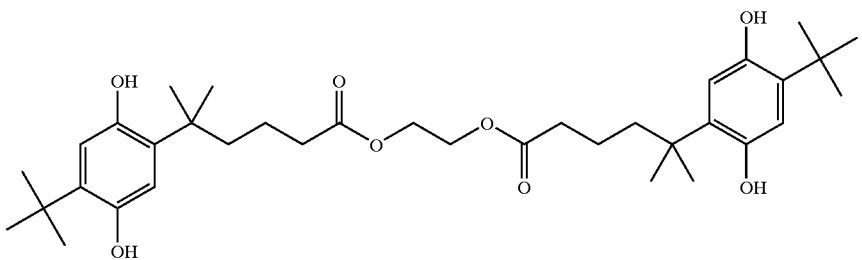
Compound 3 (invention)
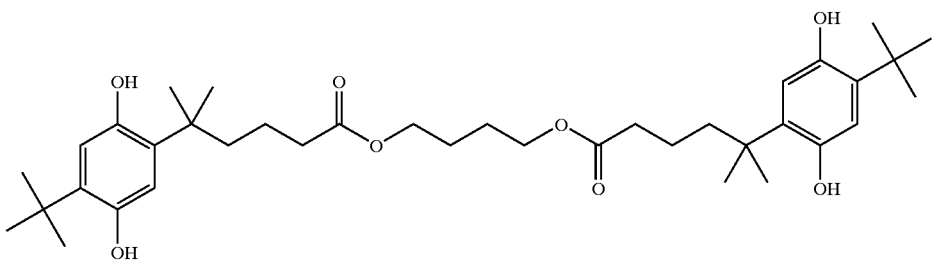
Compound 4 (invention)
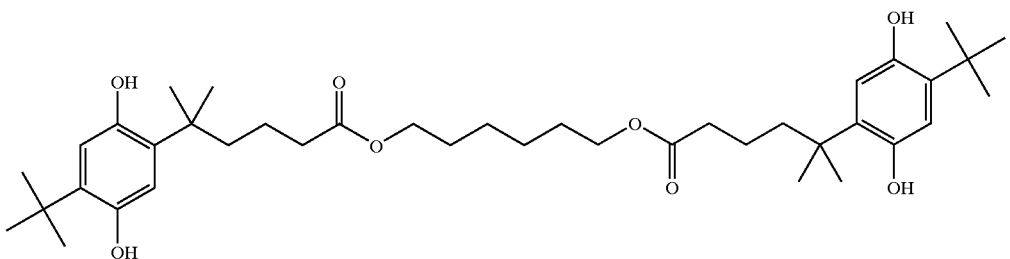

-continued
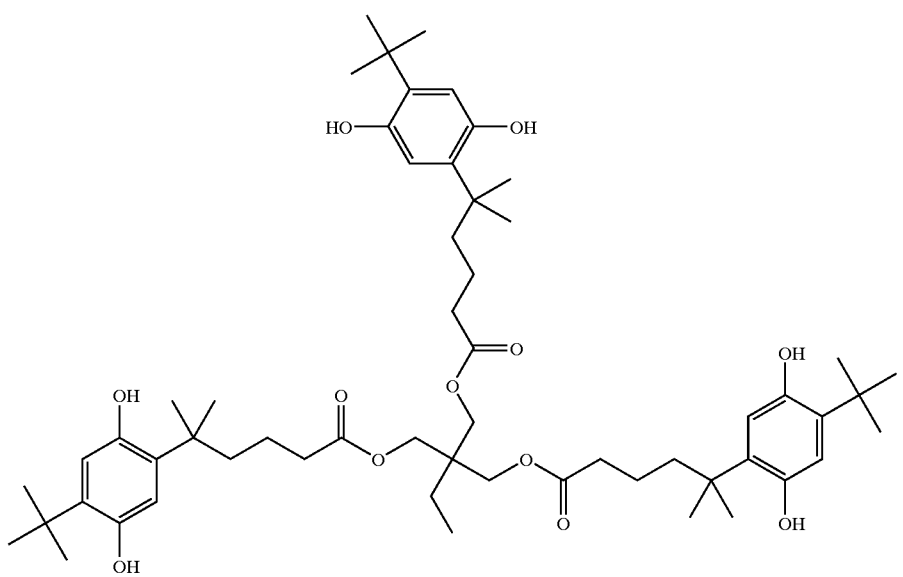
Compound 5 (invention)
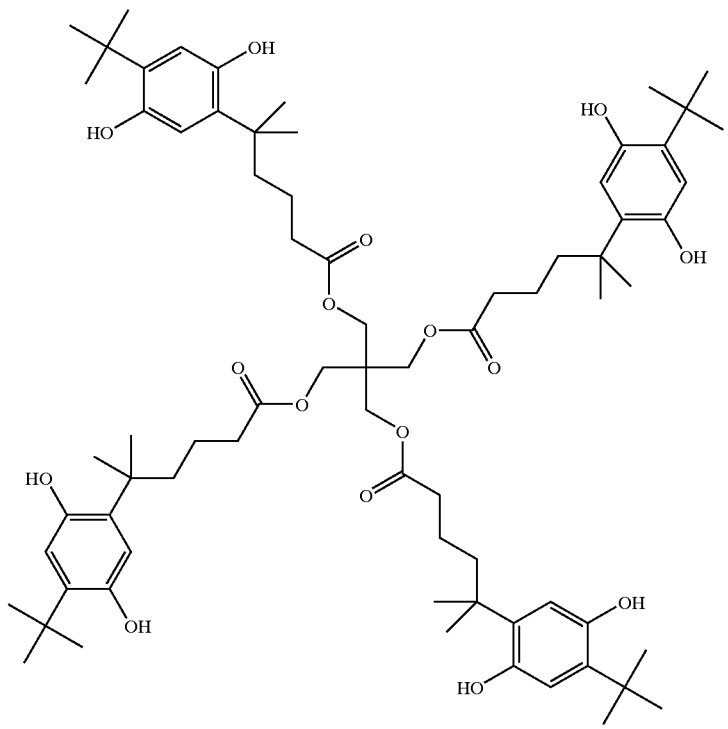
Compound 6 (invention)
The examples mentioned in the invention are prepared using the following synthetic method.
Compound 2
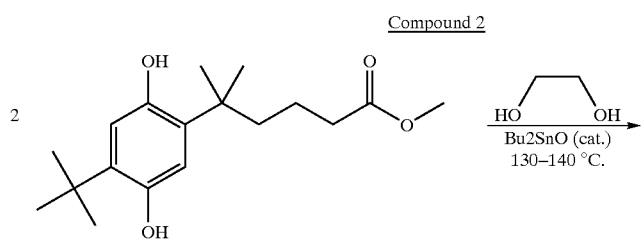

-continued

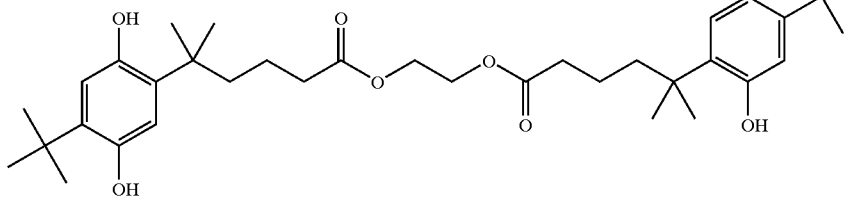

2 parts of benzenepentanoic acid, 4-(1,1-dimethylethyl)-2,5-dihydroxy-.delta.,.delta.-dimethyl-, methyl ester and 1 part of ethylene glycol are heated under a slow flow of nitrogen at 130–140° C. for 23 h. The crude product is chromatographed over silicagel (ethylacetate/hexane 2:1) to obtain a white solid, m.p. 65–70° C., yield 84%.

$^1$H-NMR (CDCl$_3$): 6.73 (s,2H), 6.51(s,2H), 4.88(s,2H, OH), 4.76(s,2H,OH), 4.23(s,4H), 2.23(t,4H), 1.78(m,4H), 1.34(s,18H),1.28(s, 12H).

Compound 3

2 parts of benzenepentanoic acid, 4-(1,1-dimethylethyl)-2,5-dihydroxy-.delta.,.delta.-dimethyl-, methyl ester and 1 part of butan-1,4-diol are heated under a slow flow of nitrogen at 130–140° C. for 23 h. The crude product is chromatographed over silicagel (ethylacetate/hexane 2:1) to obtain a light brown solid, m.p. 60–65° C., yield 73%.

$^1$H-NMR (CDCl$_3$):6.58 (s,2H), 6.52(s,2H), 4.93(s,2H, OH), 4.81(s,2H,OH), 4.12(t,4H), 2.24(t,4H), 1.78(m,4H), 1.53(m,4H),1.35 (s,18H),1.28(s,12H).

Compound 4

2 parts of benzenepentanoic acid, 4-(1,1-dimethylethyl)-2,5-dihydroxy-.delta.,.delta.-dimethyl-, methyl ester and 1 part of hexane-1,6-diol are heated under a slow flow of nitrogen at 130–140° C. for 23 h. The crude product is chromatographed over silicagel (ethylacetatelhexane 2:1) to obtain a light brown solid, m.p. 58–65, yield 70%.

$^1$H-NMR (CDCl$_3$): 6.58 (s,2H), 6.52(s,2H), 4.94(s,2H, OH), 4.88(s,2H,OH), 4.06(t,4H), 2.24(t,4H), 1.83(m,4H), 1.59(m,4H),1.36 (s,18H),1.31(s, 12H), 1.41–1.3.4(m,4H).

Compound 5

3 parts of benzenepentanoic acid, 4-(1,1-dimethylethyl)-2,5-dihydroxy-.delta.,.delta.-dimethyl-, methyl ester and 1 part of 1,1,1-tris(hydroxy methyl) propane are heated under a slow flow of nitrogen at 130–140° C. for 23 h. The crude product is chromatographed over silicagel (ethylacetate/ hexane 2:1) to obtain a light brown solid, m.p. 90° C. Yield 64%.

$^1$H-NMR (CDCl$_3$): 6.58 (s,3H), 6.47(s,3H), 5.18(s,3H, OH), 5.01(s,3H,OH), 3.93(s,6H), 2.22(t,6H), 1.78(m,6H), 1.35 (s,27H),1.26(s, 18H), 1,13 (m,2H), 0.81 (t,3H).

Compound 6

4 parts of benzenepentanoic acid, 4-(1,1-dimethylethyl)-2,5-dihydroxy-.delta.,.delta.-dimethyl-, methyl ester and 1 part of pentaerythritol are heated under a slow flow of nitrogen at 130–140° C. for 27 h. The crude product is chromatographed over silicagel (ethylacetate/hexane 2:1) to obtain a white solid, m.p. 90–95° C., yield 42%.

$^1$H-NMR (CDCl$_3$):6.58 (s,4H), 6.51(s,4H), 5.31(s,4H, OH), 5.01(s,4H,OH), 3.92(s,8H), 2.19(t,8H), 1.73(m,8H), 1.38 (s,36H),1.28(s, 24H).

APPLICATION EXAMPLES

To evaluate compounds of this invention with respect to their ability as interlayer scavengers for oxidized developing agent, three layer photographic test elements are prepared by providing layers in the order indicated on a polyethylene-coated paper support:

Test Element 1A (Check Sample)

(1) A layer containing:
   1800 mg.m$^{-2}$ of gelatin
   272 mg.m$^{-2}$ of cyan-dye-forming coupler C-1
   180 mg.m$^{-2}$ of dibutylphtalate
   2-sulfonate-4,8-diisobutyl-naphtalene, sodium salt surface active agent (2) An interlayer containing:
   1800 mg.m$^{-2}$ of gelatin
   300 mg.m$^{-2}$ of tricresylphosphate
   2-sulfonate-4,8-diisobutyl-naphtalene, sodium salt surface active agent (3) A photosensitive layer containing:
   260 mg.m$^{-2}$ (based on silver) of an unsensitized silver bromide emulsion
   1800 mg.m$^{-2}$ of gelatin
   300 mg.m$^{-2}$ of magenta-dye-forming coupler M-1
   300 mg.m$^{-2}$ of tricresylphosphate
   2-sulfonate-4,8-diisobutyl-naphtalene, sodium salt surface active agent
   2-hydroxy-4,6-dichloro-1,3,5-triazine, potassium salt hardener
   7-methyl-5-hydroxy-1,3,8-triazaindolizine antifoggant.

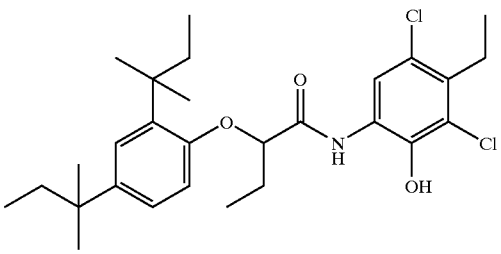

C-1

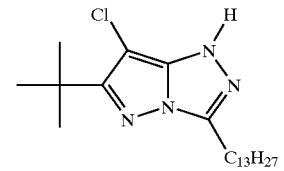

M-1

Test Elements 2A–7A (1) A layer having the same composition as the first layer of test element 1A (2) An interlayer containing
  1800 mg.m$^{-2}$ of gelatin
  20 mg.m$^{-2}$ of oxidized developer scavenger as indicated in table 1 below
  300 mg.m$^{-2}$ of tricresylphosphate
  2-sulfonate-4,8-diisobutyl-naphtalene, sodium salt surface active agent
(3) A photosensitive layer having the same composition as the photosensitive layer of test element 2A.

The test elements are imagewise exposed through a step wedge with density increment 0.15 and thereafter subjected to the AGFA P-94 developing process.

Within test elements 1A–7A, cyan dye can only be formed by the wandering of the oxidized developer from the layer in which it is formed (i.e. the uppermost layer) to the bottom layer containing the cyan-dye-forming coupler. The ability of an interlayer scavenger to prevent oxidized developer from diffusing into the bottom layer can thus be assessed by determining the cyan density at any chosen exposure amount.

The cyan density at the exposure amount giving a magenta density of 1 is reported in table 1. A cyan density which is inferior to that observed in sample 1 A indicates scavenging of the oxidized developer.

In another experiment, three layer photographic test elements are prepared by providing layers in the order indicated on a polyethylene-coated paper support:

Test Element 1B (Check Sample)
(1) A layer containing:
  1800 mg.m$^{-2}$ of gelatin
  300 mg.m$^{-2}$ of tricresylphosphate
  2-sulfonate-4,8-diisobutyl-naphtalene, sodium salt surface active agent.
(2) A photosensitive layer containing:
  260 mg.m$^{-2}$ (based on silver) of an unsensitized silver bromide emulsion
  1800 mg.m$^{-2}$ of gelatin
  300 mg.m$^{-2}$ of magenta-dye-forming coupler M-1
  225 mg.m$^{-2}$ of the magenta dye light stabilizer S-1
  300 mg.m$^{-2}$ of tricresylphosphate
  2-sulfonate-4,8-diisobutyl-naphtalene, sodium salt surface active agent
  7-methyl-5-hydroxy-1,3,8-triazaindolizine antifoggant.
(3) A layer containing:
  1800 mg.m$^{-2}$ of gelatin
  300 mg.m$^{-2}$ of tricresylphosphate
  2-sulfonate-4,8-diisobutyl-naphtalene, sodium salt surface active agent
  2-hydroxy-4,6-dichloro-1,3,5-triazine, potassium salt hardener.

Test Elements 2B–7B
(1) A layer containing:
  1800 mg.m$^{-2}$ of gelatin
  80 mg.m$^{-2}$ of oxidized developer scavenger as indicated in table 1 below
  300 mg.m$^{-2}$ of tricresylphosphate
  2-sulfonate-4,8-diisobutyl-naphtalene, sodium salt surface active agent.
(2) A photosensitive layer having the same composition as the photosensitive layer of test element 1 B.
(3) A layer containing:
  1800 mg.m$^{-2}$ of gelatin
  80 mg.m$^{-2}$ of oxidized developer scavenger as indicated in table 1 below
  300 mg.m$^{-2}$ of tricresylphosphate
  2-sulfonate-4,8-diisobutyl-naphtalene, sodium salt surface active agent
  2-hydroxy-4,6-dichloro-1,3,5-triazine, potassium salt hardener.

The test elements are imagewise exposed through a step wedge with density increment 0.30 and thereafter subjected to the AGFA P-94 developing process.

The samples obtained in this manner are stored in the dark at 60° C., 95% RH for 72 hours and thereafter evaluated for light fastness in an Atlas device equipped with a 3500 W Xenon lamp.

The light fastness of the magenta image is evaluated based on the percentage of the residual dye density after 30 kJ/cm$^2$ of light exposure (initial density=1). The results are given in table 1.

TABLE 1

| Dox scavenger | Test element | Cyan density at a magenta density of 1 | Test element | Residual dye after 30 kJ · cm$^{-2}$ of Atlas exposure (%) (72 h dark storage at 60° C., 95% RH prior to Atlas exposure) |
|---|---|---|---|---|
| none (check) | 1A | 0.227 | 1B | 75 |
| Compound 1 (comparison) | 2A | 0.180 | 2B | 60 |
| Compound 2 (invention) | 3A | 0.173 | 3B | 34 |
| Compound 3 (invention) | 4A | 0.173 | 4B | 38 |
| Compound 4 (invention) | 5A | 0.179 | 5B | 56 |
| Compound 5 (invention) | 6A | 0.171 | 6B | 68 |

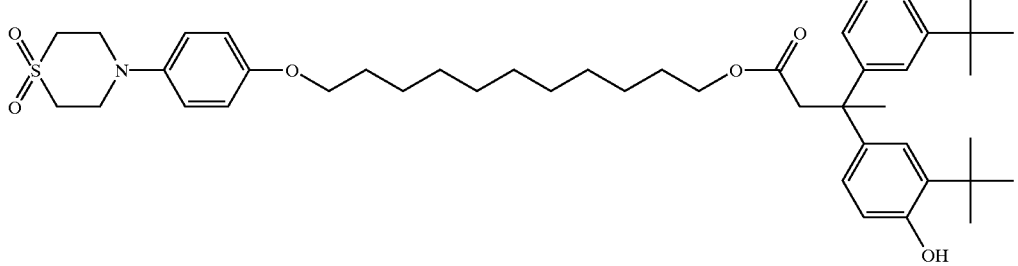

S-1

TABLE 1-continued

| Dox scavenger | Test element | Cyan density at a magenta density of 1 | Test element | Residual dye after 30 kJ · cm$^{-2}$ of Atlas exposure (%) (72 h dark storage at 60° C., 95% RH prior to Atlas exposure) |
|---|---|---|---|---|
| Compound 6 (invention) | 7A | 0.174 | 7B | 69 |

It is clear from the data in table 1 that compounds within the scope of this invention are very effective in preventing the oxidized developer from wandering and forming dye in the wrong layer and even provide superior protection against color contamination when compared to the comparison compound 1. Furthermore, compounds 5 and 6 according to this invention are substantially less detrimental to the light resistance of the magenta image than the comparison compound 1.

What is claimed is:

1. A compound of the formula I

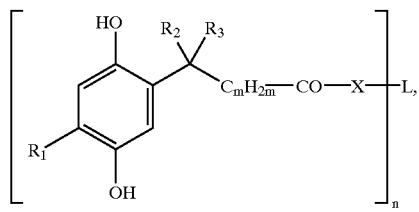

where n is 2–50;

X is O or NR$_4$;

if n is 2,

L is C$_2$–C$_{25}$-alkylene; C$_4$–C$_{25}$-alkylene interrupted by O, S or

C$_5$–C$_{12}$ cycloalkylene; or a group phenylene, naphthylene,

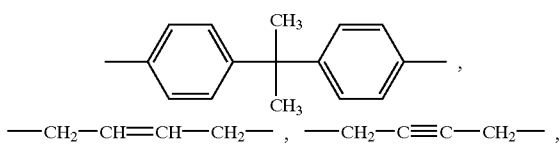

—CH$_2$—CH═CH—CH$_2$—, —CH$_2$—C≡C—CH$_2$—, each of which may be unsubstituted or substituted by C$_1$–C$_4$-alkyl;

if n is 3, L is

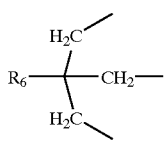

when n is 4, L is

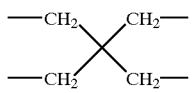

when n is >4, L is a residue of a C$_5$ or C$_6$ sugar or a polymeric chain such as a polyvalent residue of a polyvinyl alcohol R$_1$ is H, halogen, C$_1$–C$_{25}$-alkyl, C$_3$–C$_{25}$-alkenyl, unsubstituted or by C$_1$–C$_4$-alkyl substituted C$_5$–C$_8$-cycloalkyl;

R$_2$ and R$_3$ independently of each other are C$_1$–C$_4$alkyl, or together with the carbon atom they are bonded to, form a carbocyclic C$_5$–C$_7$ ring, especially C$_5$–C$_7$cycloalkylene;

R$_4$ is H or C$_1$–C$_{18}$alkyl,

R$_5$ is H or C$_1$–C$_{18}$alkyl or C$_1$–C$_{25}$alkanoyl,

R$_6$ is C$_1$–C$_{18}$alkyl or —NR$_7$R$_8$;

R$_7$, R$_8$ independently are C$_1$–C$_{18}$alkyl or C$_1$–C$_{25}$alkanoyl, and m is 1–20.

2. A compound according to claim 1 of the formula I'

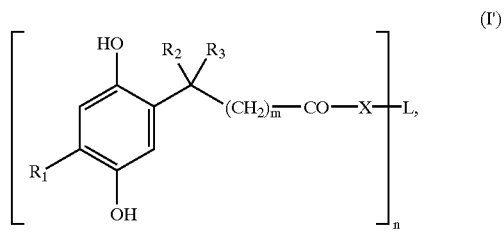

where n is 2–30;

R$_1$ is C$_1$–C$_{25}$alkyl,

R$_2$ and R$_3$ independently are C$_1$–C$_4$alkyl, or together with the bonding carbon atom are C$_5$–C$_7$cycloalkylene, R$_4$ is H, R$_5$ is H, R$_6$ is C$_1$–C$_{18}$alkyl, R$_7$, R$_8$ independently are C$_1$–C$_{18}$alkyl or C$_1$–C$_{25}$alkanoyl, m is 2–4.

3. Process for preventing migration of the oxidized developer in a color photgraphic material from one color sensitive layer to another by incorporating a compound of the formula I according to claim 1 into said material.

4. A color photographic material containing a compound of formula I according to claim 1.

5. A color photographic material according to claim 4, containing the compound of the formula I in a non-photsensitive interlayer.

6. A color photographic material according to claim 4, containing the compound of the formula I in an amount from 10 to 1000 mg/m$^2$.

* * * * *